(12) United States Patent
Davies (10) Patent No.: US 8,308,720 B2
(45) Date of Patent: Nov. 13, 2012

(54) CARDIAC ELECTROSURGERY

(75) Inventor: Gareth Davies, Toronto (CA)

(73) Assignee: Baylis Medical Company Inc., Montreal (CA)

( * ) Notice: Subject to any disclaimer, the term of this patent is extended or adjusted under 35 U.S.C. 154(b) by 1322 days.

(21) Appl. No.: 12/005,316

(22) Filed: Dec. 27, 2007

(65) Prior Publication Data

US 2008/0208184 A1 Aug. 28, 2008

Related U.S. Application Data

(60) Provisional application No. 60/883,074, filed on Jan. 2, 2007.

(51) Int. Cl.
*A61B 18/18* (2006.01)
(52) U.S. Cl. .................... 606/34; 606/41; 606/45
(58) Field of Classification Search .......... 606/32–41
See application file for complete search history.

(56) References Cited

U.S. PATENT DOCUMENTS

| | | | | |
|---|---|---|---|---|
| 5,056,526 A | * | 10/1991 | Khalil | 600/505 |
| 5,385,156 A | * | 1/1995 | Oliva | 128/898 |
| 5,536,242 A | * | 7/1996 | Willard et al. | 604/30 |
| 5,665,085 A | | 9/1997 | Nardella | |
| 5,766,164 A | * | 6/1998 | Mueller et al. | 606/15 |
| 5,893,848 A | * | 4/1999 | Negus et al. | 606/41 |
| 6,092,526 A | * | 7/2000 | LaFontaine et al. | 128/898 |
| 6,161,543 A | | 12/2000 | Cox et al. | |
| 6,314,963 B1 | | 11/2001 | Vaska et al. | |
| 6,780,178 B2 | * | 8/2004 | Palanker et al. | 606/34 |
| 6,786,906 B1 | | 9/2004 | Cobb | |
| 6,889,077 B2 | * | 5/2005 | Bornzin et al. | 607/4 |
| 6,918,890 B2 | * | 7/2005 | Schmidt | 604/164.01 |
| 2005/0273129 A1 | * | 12/2005 | Michels et al. | 606/185 |

OTHER PUBLICATIONS

Eduardo Sosa, Mauricio Scanavacca, Andre D'Avila, Flavio Oliveira, Jose Antonio F. Ramires, "Nonsurgical transthoracic epicardial catheter ablation to treat recurrent ventricular tachycardia occurring late after myocardial infarction", "Journal of the American College of Cardiology", May 2000, pp. 1442-1449, vol. 35, No. 6, Publisher: Elsevier Science Inc., Published in: US.

Miguel Valderrabano, David A. Cesario, Sen Ji, Kevin Shannon, Isaac Wiener, Charles D. Swerdlow, Hakan Oral, et al., "Percutaneous epicardial mapping during ablation of difficult accessory pathways as an alternative to cardiac surgery", Sep. 2004, pp. 311-316, vol. 1, No. 3, Publisher: Heart Rhythm Society, Published in: US.

* cited by examiner

*Primary Examiner* — Linda Dvorak
*Assistant Examiner* — Amanda Scott (57) ABSTRACT

A method of accessing a pericardial cavity of a heart is disclosed, comprising delivering electrical energy to a pericardium in a manner which creates a channel substantially through a parietal pericardium and does not substantially affect myocardial tissue.

24 Claims, 7 Drawing Sheets

CARDIAC ELECTROSURGERY

CROSS-REFERENCES TO RELATED APPLICATIONS

The present application claims the benefit of U.S. provisional patent application 60/883,074, filed on Jan. 2, 2007, incorporated herein by reference.

TECHNICAL FIELD

The present invention relates to methods for treating the heart of a patient. More specifically, the present invention relates to methods of accessing the pericardial cavity of a patient's heart.

BACKGROUND OF THE ART

The pericardium is the outermost layer of the heart, surrounding the myocardium. The pericardium consists of two layers: an outer fibrous layer, and an inner serous layer. The inner serous layer is further sub-divided into two layers: an outer parietal layer, and an inner visceral layer. The inner visceral layer is referred to as the epicardium, and immediately covers the myocardium and the great vessels of the heart. Situated between the parietal layer and the epicardium is the pericardial cavity, a fluid-filled space typically containing approximately 20-25 mL of physiological fluid.

Certain cardiac conditions are treated by percutaneously inserting a needle through the outer layers of the pericardium into the pericardial cavity, and performing a treatment procedure from within the pericardial cavity. For example, ventricular tachycardia is often treated by inserting a needle into the pericardial cavity to provide access to the epicardium for catheter mapping and ablation procedures (Valderrabano et al. (2004), Heart Rhythm 1 (3):311-6; Sosa et al. (2000) J Am Coll Cardiol 35:1442-9). This technique uses a standard epidural needle, which is inserted into the subxiphoid region, to puncture both the thoracic cavity and the outer layers of the pericardium. Once the needle has reached the pericardial cavity, catheter mapping and ablation procedures are performed on the epicardium.

This technique, however, has various risks associated with it, the most notable of which is the laceration of the myocardium by the needle. This risk is heightened in cases where the pericardial cavity and fluid volume is small. One report found accidental right ventricular laceration occurred in greater than 7% of patients (Sosa et al. (2000) J Am Coll Cardiol 35:1442-91.

U.S. Pat. Nos. 6,161,543, issued on Dec. 19, 2000 to Cox et al., and 6,314,963, issued on Nov. 13, 2001 to Vaska et al., both describe alternative methods of accessing the pericardial cavity, but the methods described therein are relatively invasive and carry further risks to the patient.

Thus, a method for accessing the pericardial cavity which may overcome some or all of the deficiencies of the prior art is desired.

DETAILED DESCRIPTION

In accordance with one broad aspect of the present invention, a method for accessing the pericardial cavity of the heart of a human or animal is provided. In some embodiments, the method comprises delivering electrical energy to a pericardium in a manner which creates a channel substantially through a parietal pericardium and does not substantially affect myocardial tissue. As used herein, the parietal pericardium refers to the outer layers of the pericardium, including both the fibrous pericardium as well as the parietal layer described above.

As a feature of this aspect, in some embodiments, the delivery of electrical energy is effected for a time period of less than about 1.0 seconds and, in particular embodiments, between about 0.2 and 0.8 seconds.

As further features of this aspect, in some embodiments, the energy is delivered in response to a signal indicative of a cardiac cycle of the patient's heart, such as an electrocardiogram. In some such embodiments, the energy is delivered in response to a P-wave of the electrocardiogram while, in other such embodiments, the energy is delivered in response to a T-wave of the electrocardiogram. In addition, in some embodiments, the energy is delivered substantially during diastole and is substantially not delivered during systole of the patient's cardiac cycle.

In some embodiments, the method further comprises determining a presence of the channel by delivering a contrast fluid after delivering energy. In some particular embodiments, the contrast fluid is delivered via the device used to deliver the electrical energy.

In another aspect of the present invention, a method of accessing a pericardial cavity of a heart is provided, the method comprising: (a) delivering electrical energy to a pericardium in a manner which creates a channel at least partially through a parietal pericardium and does not substantially affect myocardial tissue; and (b) repeating (a) until a channel is formed substantially through the parietal pericardium As a feature of this aspect, the delivery of the electrical energy is effected by an electrosurgical device and the electrosurgical device is further used for aspirating fluid after (a). In alternate embodiments, the method further comprises a step of measuring pressure exerted on a distal portion of the electrosurgical device prior to (b).

As a further aspect of the present invention, some embodiments include a method of epicardial ablation, comprising: delivering electrical energy via an electrosurgical device to a pericardium in a manner which creates a channel substantially through a parietal pericardium to a pericardial cavity; and delivering electrical energy to create a lesion in the epicardium.

As a feature of this aspect, in some embodiments, the electrosurgical device is used for delivering the electrical energy as well as creating the lesion. As an additional feature, the electrosurgical device comprises at least one perforation electrode for creating the channel and at least one ablation electrode for creating the lesion.

As a further aspect of the present invention, some embodiments include a method of cardiac electrosurgery, the method comprising: inserting an electrosurgical device substantially adjacent to a patient's heart; measuring an electrocardiogram of the patient's heart; and delivering high-frequency electrical energy to treat at least a portion of the patient's heart; wherein the delivery of the high-frequency electrical energy is responsive to one or more portions of the measured electrocardiogram.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Theory

As used herein, 'perforation' refers to a procedure in which energy is applied from a device to a tissue to create a perforation, void, or channel through the tissue. The energy may be electrical current in the radiofrequency or microwave range, or the energy may be in the form of ultrasonic vibration, for example.

In the case of electrical current, and without being limited to a particular theory of operation, it is believed that during a perforation procedure the current serves to rapidly increase tissue temperature to the extent that water in the intracellular fluid becomes converted to steam, inducing cell lysis as a result of elevated pressure within the cell. Furthermore, electrical breakdown may occur between the cell and the electrode, wherein the electric field induced by the alternating current exceeds the threshold dielectric strength of the medium located between the electrode and the cell, causing a dielectric breakdown. This in turn may lead to electrical arcing which results in rapid cellular heating and cellular rupture. In addition, mechanical breakdown may occur, wherein an alternating current induces stresses on polar molecules in the cell, resulting in electroporation. Upon the occurrence of cell lysis and rupture, a void is created, allowing the device to advance into the tissue with little resistance. In order to achieve this effect, the device from which energy is applied, i.e. the electrode, must be relatively small, in order to increase the current density delivered to the tissue. In addition, the energy source must be capable of applying a high voltage, for example about 1600V Peak, through both a low impedance as well as a high impedance load, for example through about 300 ohms up to about 10000 ohms. Further details regarding the theory of radiofrequency perforation and systems suitable for radio-frequency perforation may be found in U.S. patent application Ser. No. 11/265,304, filed on Nov. 3, 2005, and in U.S. patent application Ser. No. 11/520,754, filed on Sep. 14, 2006, both of which are incorporated herein by reference.

In the case of ultrasonic vibration, it is believed that mechanical vibrations pulverize tissue by mechanical impact, creating a channel through the tissue. In addition to direct mechanical perforation, high frequency vibration can create vapour-filled micro-bubbles which then expand and implode producing cavitations and liquid jets that can break cellular molecular bonds and erode the tissue.

Device

An example of a suitable device for use with embodiments of a method of the present invention will presently be described. It is to be noted, however, that the devices described herein are meant to be illustrative only.

Referring to FIG. 1, embodiments of an exemplary perforation device 100 for creating a channel through a tissue comprises an elongate member 102 having a proximal region 104 ending in a proximal end 106, and a distal region 108 ending in a distal end 110. As used herein, the terms 'proximal' and 'distal' are defined with respect to the user. That is, the term 'proximal' refers to a part or portion closer to the user, and the term 'distal' refers to a part or portion further away from the user, when the device is in use. An energy delivery device 112 is disposed at distal end 110 for delivering energy to the tissue to create a channel therethrough. The energy delivery device may be an electrically conductive and exposed component for delivering electrical current, i.e. an electrode, or the energy delivery device may be structured for delivering vibrational energy, for example. In embodiments comprising an energy delivery device for delivering vibrational energy, the vibrational energy may be produced by an ultrasonic transducer located outside the patient's body and the vibrational energy may then be transmitted to the tissue via a means for transmitting vibrations, for example a wire and, more specifically, a nitinol wire. Alternatively, the energy delivery device may comprise an ultrasonic transducer disposed at distal end 110 of device 100.

Figure 1A:
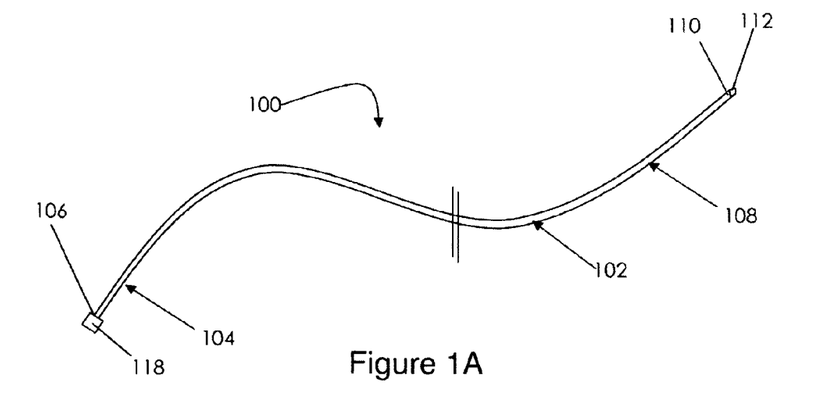
FIG. 1A is a perspective illustration of an embodiment of a perforation device that may be used in accordance with a method of the present invention.
Figure 1B:
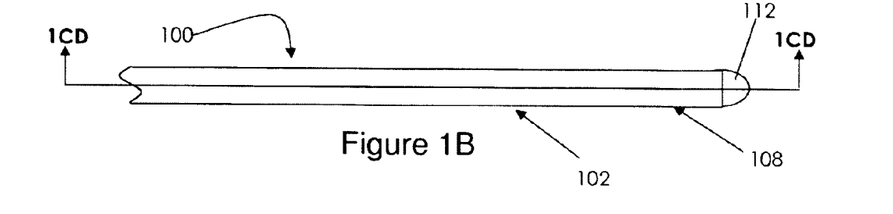
FIG. 1B is a partial plan view of an embodiment of a perforation device that may be used in accordance with a method of the present invention.
Figure 1C:
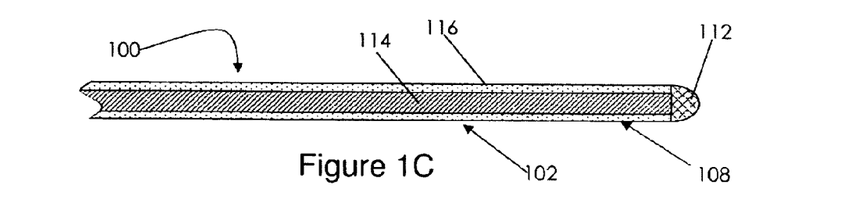
FIGS. 1C-1D are various embodiments of partial longitudinal cross-sectional views along the line 1CD-1CD in FIG. 1B.

In some embodiments, distal end 110 may be substantially atraumatic to reduce the risk of accidental myocardial puncture and/or laceration. As shown in FIG. 1C, elongate member 102 may comprise an electrically conductive wire 114 for operatively coupling energy delivery device 112 to a source of energy. Wire 114 may be coated with an electrically insulative coating 116, which may extend proximally from energy delivery device 112, as shown in FIG. 1C. Wire 114 may be coupled to energy delivery device 112 by welding, or soldering, for example. In the illustrated embodiment, proximal end 106 comprises a hub 118 for operatively coupling device 100 to an energy source.

Figure 1D:
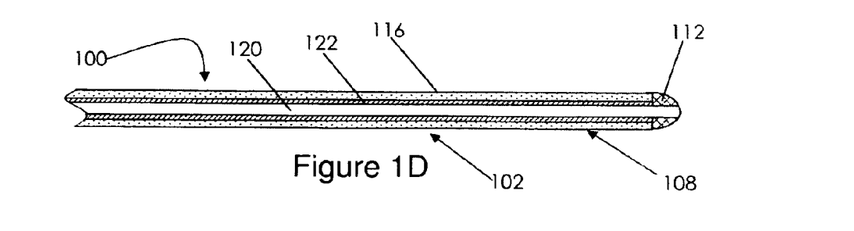

In some embodiments, device 100 may define a lumen 120 therethrough, as shown for example in FIG. 1D, such that material may be injected and/or withdrawn through distal end 110. In such embodiments, rather than a wire 114, elongate member may comprise a hollow conductive tube 122. Alternatively, device 100 may comprise a hollow insulated tube, for example a catheter, with a conductive wire embedded in a wall thereof.

Device 100 may further have various sensors associated therewith. For example, distal end 110 may comprise an impedance sensor, a temperature sensor, and/or a pressure sensor.

Figure 1E:
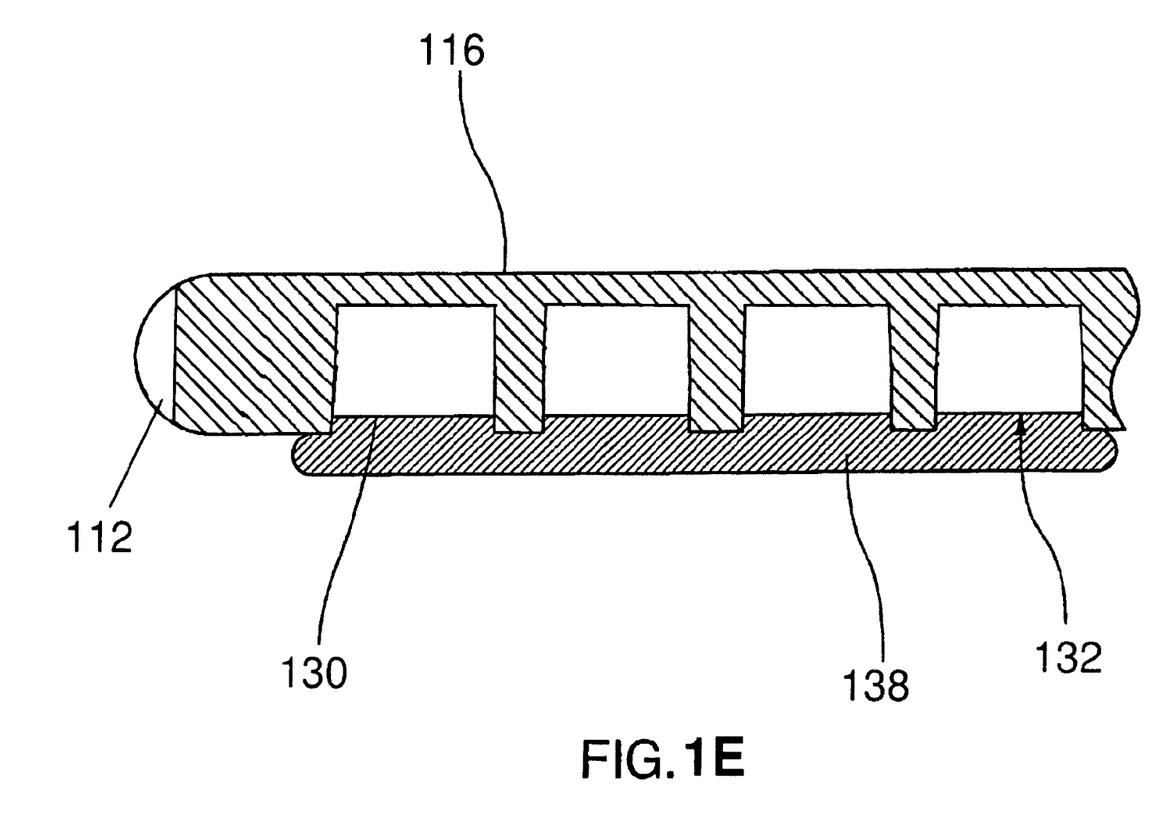
FIG. 1E is a side elevation view of an alternate embodiment of a perforation device that may be used in accordance with a method of the present invention.

In an alternate embodiment, a device used to perform a method of the present invention comprises a plurality of electrodes, for example at least one perforation electrode and at least one ablation electrode. An example of such an embodiment is illustrated in FIG. 1E, which shows a device including a perforation electrode 112 located at a distal end of the device, as well as a plurality of ablation electrodes 130, which may also be referred to as "windows of conductivity" 132. As described herein above, perforation electrodes typically have a smaller surface area when compared to ablation electrodes, and may be used to create a channel through tissue by the delivery of high-frequency electrical energy. Ablation electrodes, on the other hand, are typically larger and may be used to create one of more lesions in a tissue. Such a device may be particularly suitable for embodiments of a method of the present invention involving ablation of the epicardium 138, as will be described further herein below. Further details regarding similar devices may be found in U.S. application Ser. No. 11/381,783, filed on May 5, 2006, incorporated herein by reference. In some embodiments, the same electrode is used for both perforation as well as ablation. For example, the surface area of the electrode may be altered during the course of the procedure to enable the electrode to create both a channel through tissue as well as a lesion. Alternatively, or in addition, the parameters of energy delivery may be altered such that both perforation and ablation are effected by a single electrode.

Further examples of suitable devices for creating a channel through a tissue by the delivery of energy include the Power-Wire™ Radiofrequency (RF) Guidewire of Baylis Medical Company Inc. (Montreal, Canada), the Toronto Trans-septal Catheter of Baylis Medical Company Inc. (Montreal, Canada), as well as the Radiofrequency Perforation Device described in U.S. Provisional Patent Application 60/827,452 (filed on Sep. 29, 2006) and the apparatus described in U.S. patent application Ser. No. 11/905,447, filed on Oct. 1, 2007, entitled "Radiofrequency Perforation Apparatus", incorporated herein by reference. An example of an energy source suitable for use with a perforation device is the Radiofrequency Puncture Generator of Baylis Medical Company Inc. (Montreal, Canada).

Method

In one aspect, a method of the present invention comprises a method of accessing a pericardial cavity of a heart, the method comprising delivering electrical energy to a pericardium in a manner which creates a channel substantially through a parietal pericardium and does not substantially affect myocardial tissue.

An exemplary embodiment of this aspect comprises the steps of: delivering energy through an energy delivery device to an outer surface of a pericardium of a patient's heart, where the outer surface refers to the outermost layer of the pericardium; advancing the energy delivery device through the outer surface and through the parietal pericardium of the patient's heart; and stopping the delivery of energy when the energy delivery device has reached the pericardial space; whereby a channel is created from the outer surface of the pericardium to the pericardial cavity. Although the energy delivery device may be any device suitable for perforation as described above, an exemplary embodiment of the method will be presently described with reference to an active electrode as the energy delivery device used to create the perforation.

Prior to delivering energy to the pericardium, a number of steps may be performed. For example, various treatment compositions or medicaments, such as antibiotics or anesthetics, may be administered to the patient, and various diagnostic tests, including imaging, may be performed.

Various approaches to insertion of an electrosurgical device may be required, depending on the particular procedure being performed. In one particular application of a method of the present invention, for example when treating epicardial arrhythmias such as ventricular tachycardia, the patient is placed in the supine position, for example on an operating table, and the entry site on the patient's skin is cleaned and disinfected. In some embodiments, the entry site is located at the subxiphoid region of the patient's thorax.

In another application of a method of the present invention, for example when performing a pericardiocentesis procedure, the following approach may be used: the patient should sit at 30-45° head elevation, which increases pooling of fluid toward the inferior and anterior surface, thus Maximizing fluid drainage. The entry site in such applications may be the subxiphoid region, on the left side.

Once the entry site has been determined, in some embodiments, an introducer apparatus is used to puncture the thorax. The introducer apparatus may comprise, for example, a cannula housing a removable obturator. The cannula may be sized to house a perforation device such as the electrosurgical devices described hereinabove, as well as a sheath and/or dilator, as will be described hereinbelow. The obturator may have a sharp distal end for piercing tissue. In some such embodiments, the introducer apparatus is inserted between the left border of the xiphoid process and the lower left rib, at an angle of approximately 45° towards the left scapula. In other embodiments, depending on the target location on the pericardium, the physician or user may adjust the orientation and positioning of the introducer as they see fit. For example, when performing a pericardiocentesis procedure, the needle is typically advanced toward the shoulder at an angle 15-20° from the abdominal wall.

When the distal tip of the introducer apparatus has penetrated the subcutaneous tissue, the user may remove the obturator from the cannula. This may aid in preventing damage to tissues and organs as the cannula is advanced through the thorax towards the heart. If the obturator is removed at this point of the procedure, a perforation device, for example as described hereinabove, may be inserted into the cannula. Alternatively, the perforation device may be inserted into the cannula later in the procedure.

In some embodiments, fluoroscopy is used to visualize the position of the cannula as it is advanced towards the heart. In one particular embodiment, the cannula is visualized from the left anterior oblique view at approximately 35-40°. Fluoroscopic visualization may be enhanced by incorporation of a radiopaque marker on one or more of the cannula, the obturator and/or the perforation device. In addition, the user may inject a contrast solution through the cannula or through a lumen of the perforation device as they are being advanced towards the heart. In some embodiments, the cannula is advanced slowly towards the right ventricular apex of the heart (because it is mostly devoid of vessels).

Typically, the cannula is advanced until the distal end is substantially adjacent the pericardium. For example, using fluoroscopy, the cannula may be advanced within a few centimeters from the cardiac silhouette and then properly positioned for puncture of the pericardial sac. In addition to visualization, the user may discern when the cannula has reached the appropriate position by feeling a slight negative pressure due to the beating of the heart. That is, as the heart contracts, the user may feel a slight 'pulling' on the cannula. Alternatively, or in addition, fluoroscopy may reveal a V-shaped indentation (or "tenting") of the pericardium with contrast injection if the cannula is pressed against the pericardium.

FIGS. 2A-2F show a portion of a patient's heart including a pericardium 226, a myocardium 228, and a ventricle 230. Pericardium 226 comprises a fibrous pericardium 232, a parietal layer 234, a pericardial cavity 236, and an epicardium 238.

Figure 2A:
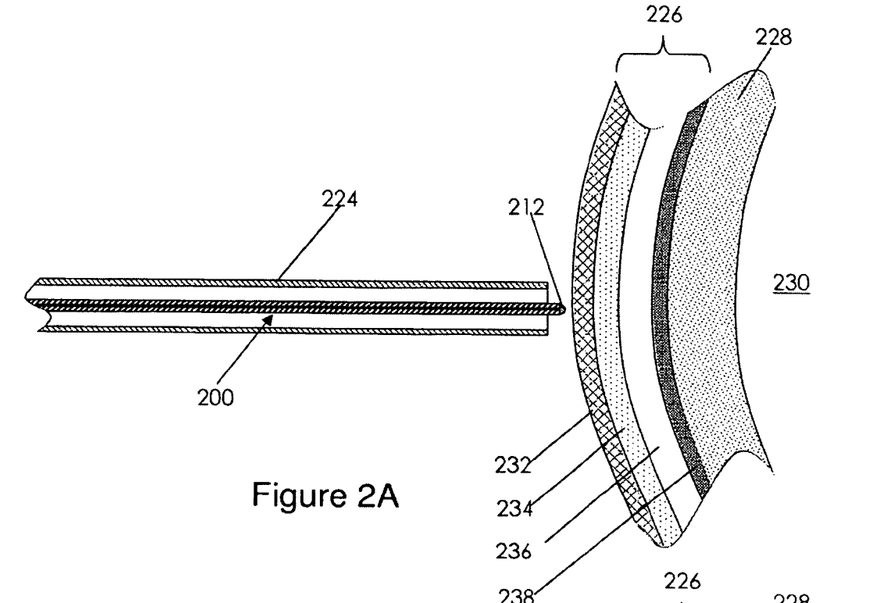
FIGS. 2A-2F are cross-sectional illustrations of the steps of one embodiment of a method of the present invention.

Referring to FIG. 2A, once the cannula 224 has reached the appropriate position proximate to the heart, the distal end of cannula 224 may be positioned at the target site, which, in some embodiments, is on, at, or adjacent to the surface of the fibrous pericardium 232. Again, this may be facilitated by using fluoroscopic visualization or any other suitable medical imaging modality (for example, ultrasound, CT or MRI). The location of the target site may depend on numerous factors, including the nature of the procedure to be performed from within the pericardial space, and the specific anatomy of the patient's heart. For example, if the procedure to be performed is ablation of an epicardial re-entry site, the target site may be the portion of the pericardium above the medial third of the right ventricle. Alternatively, if the procedure to be performed is pericardiocentesis, the target site may be near the apex of the heart.

Once the distal end of cannula 224 has been positioned at the target site, the perforation device 200 may be inserted into cannula 224, if this was not previously done. Perforation device 200 may be any device from which energy is applied to create a perforation, void, or channel through the tissue, including, but not limited to, electrosurgical device 100 of FIG. 1. Perforation device 200 may be inserted and positioned such that the energy delivery device 212 is located at the distal end of cannula 224, for example in contact with the outer surface of the pericardium at the target site. In some embodiments, the patient may be asked to hold their breath, for example in order to limit respiratory movement.

Prior to the delivery of energy, a dispersive return electrode may be operatively coupled to the patient's body. In some embodiments, the dispersive return electrode may comprise a grounding pad, which may be placed on the skin of the patient. In alternate embodiments, the perforation device may be operable in a bipolar manner, in which case a dispersive electrode is not required. A bipolar device may be further beneficial in that the energy delivered via the perforation device would remain concentrated around the two electrodes, substantially limiting the flow of current through undesirable structures such as the heart. Alternatively, if the energy delivery device comprises an ultrasonic transducer, a dispersive electrode would similarly not be required.

Figure 2B:
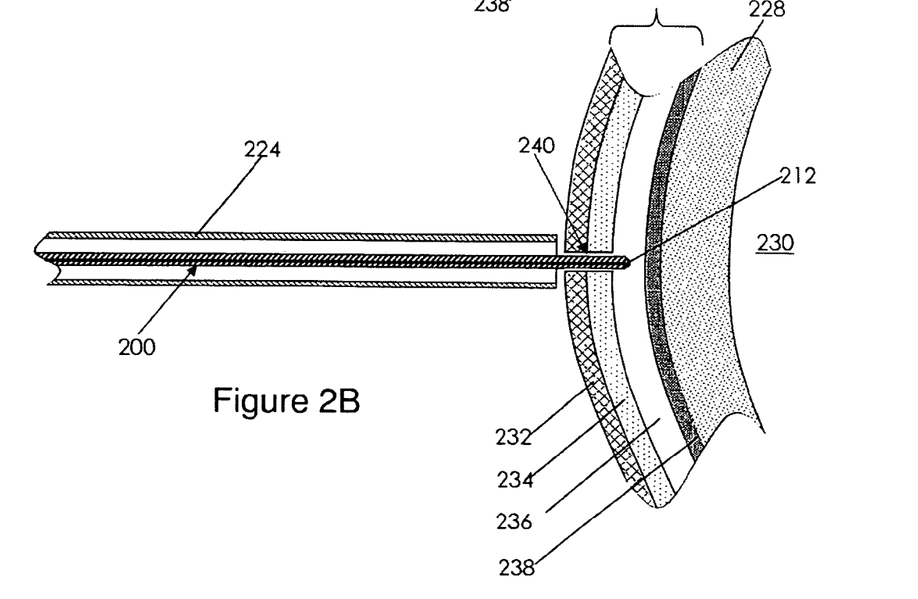

Referring now to FIG. 2B, a channel 240 is created through the outer layers 232, 234 of the pericardium by delivering energy from an energy source, such as a generator as described hereinabove, through energy delivery device 212 of perforation device 200, to the tissue of the pericardium. In some embodiments, wherein energy delivery device 212 comprises an active electrode, the energy delivered may be radiofrequency energy in the form of a sine wave, and may be at a voltage of between about 70V and about 1000V peak. In some embodiments, the user applies forward force to perforation device 200 as energy is being delivered, such that perforation device 200 advances through the tissue as channel 240 is created.

More particularly, the following procedure may be performed in order to create channel 240 through the outer layers 232, 234 of the pericardium. Slight forward pressure may be applied until the user, using tactile feedback, feels the heart pressing against the perforation device. The device is then pulled back slightly until the heart is no longer felt, at which point radiofrequency energy, for example, is delivered to create channel 240. Alternatively, as described hereinabove, the perforation device may be advanced until slight 'tenting' of the pericardium is visible under fluoroscopy without reaching the epicardium, at which point the electrical energy is delivered.

Following the delivery of energy, the position of the perforation device may be confirmed and, if the channel 240 has been created substantially through to the pericardial cavity, the perforation device may be advanced slightly, taking care not to press against the epicardium (using, for example, tactile feedback or an electrocardiogram (ECG) to indicate when the perforation device is contacting the epicardium, where the ECG typically shows an injury response if the heart is contacted), and the delivery of energy may be repeated.

Alternatively, rather than advancing perforation device 200 while delivering energy, the user may position energy delivery device 212 and time the delivery of energy such that the beating motion of the heart forces the pericardium against perforation device 200, thereby causing perforation device 200 to advance into the pericardium. For example, the user may deliver energy during diastole, such that the heart expands towards the device, rather than physically advancing the device through the pericardium.

More specifically, in some such embodiments, the user may deliver energy in response to a signal indicative of a cardiac cycle of the heart, such as an electrogram or electrocardiogram. Such an approach may be particularly beneficial when the level of fluid within the pericardial cavity is relatively normal, such that the space between parietal pericardium and the epicardium is relatively small. For example, procedures involving epicardial ablation may benefit from such an approach. In some such embodiments, the delivery of energy may be timed to occur in response to a particular feature of the cardiac cycle, as measured by the ECG signal. Timing the delivery of energy in response to the ECG signal may also be referred to as triggering or gating off of the ECG signal.

Figure 3:
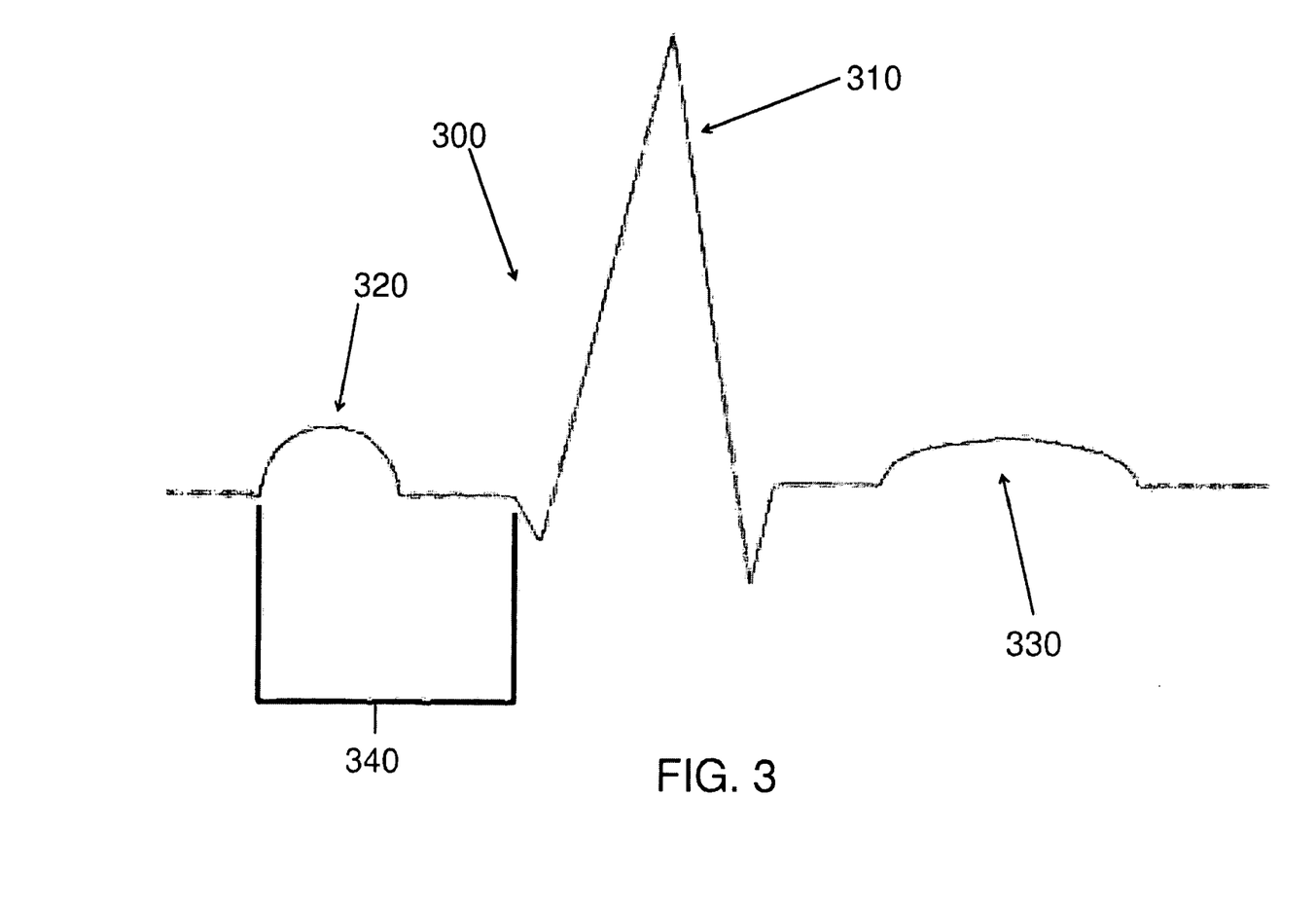
FIG. 3 is an illustration of a single cycle of a typical electrocardiogram (ECG) signal.

FIG. 3 is an illustration of a single cycle of a typical ECG signal 300. Typically, the feature of the ECG signal that is used for triggering is the QRS complex 310, as it generally has the highest amplitude. In some embodiments, the perforation energy should be delivered when the portion of the myocardium nearest the target site on the outer surface of the pericardium is furthest away from the perforation device, thereby reducing the risk of damaging or otherwise adversely affecting the myocardial tissue. For example, if the procedure involves ablating a location on a ventricle, energy may be delivered at least partially concurrently with the ejection of blood from the ventricles, which is indicated by T-wave 330 on ECG signal 300. Alternatively, if an ablation site is located on an atrium, the energy may be delivered at least partially concurrently with the ejection of blood from the atria and the filling of the ventricles, which is indicated by P-wave 320 on ECG signal 300. The period of time between the P-wave 320 and the R-wave of the QRS complex 310 is indicated by reference number 340 on FIG. 3. In order to deliver energy at least partially concurrently with the P- or T-waves, a user may adjust a delay of the trigger signal off of the QRS complex such that it causes energy to be delivered at the appropriate time. This delay would depend on the particular cardiac cycle of the patient being treated.

Figure 4:
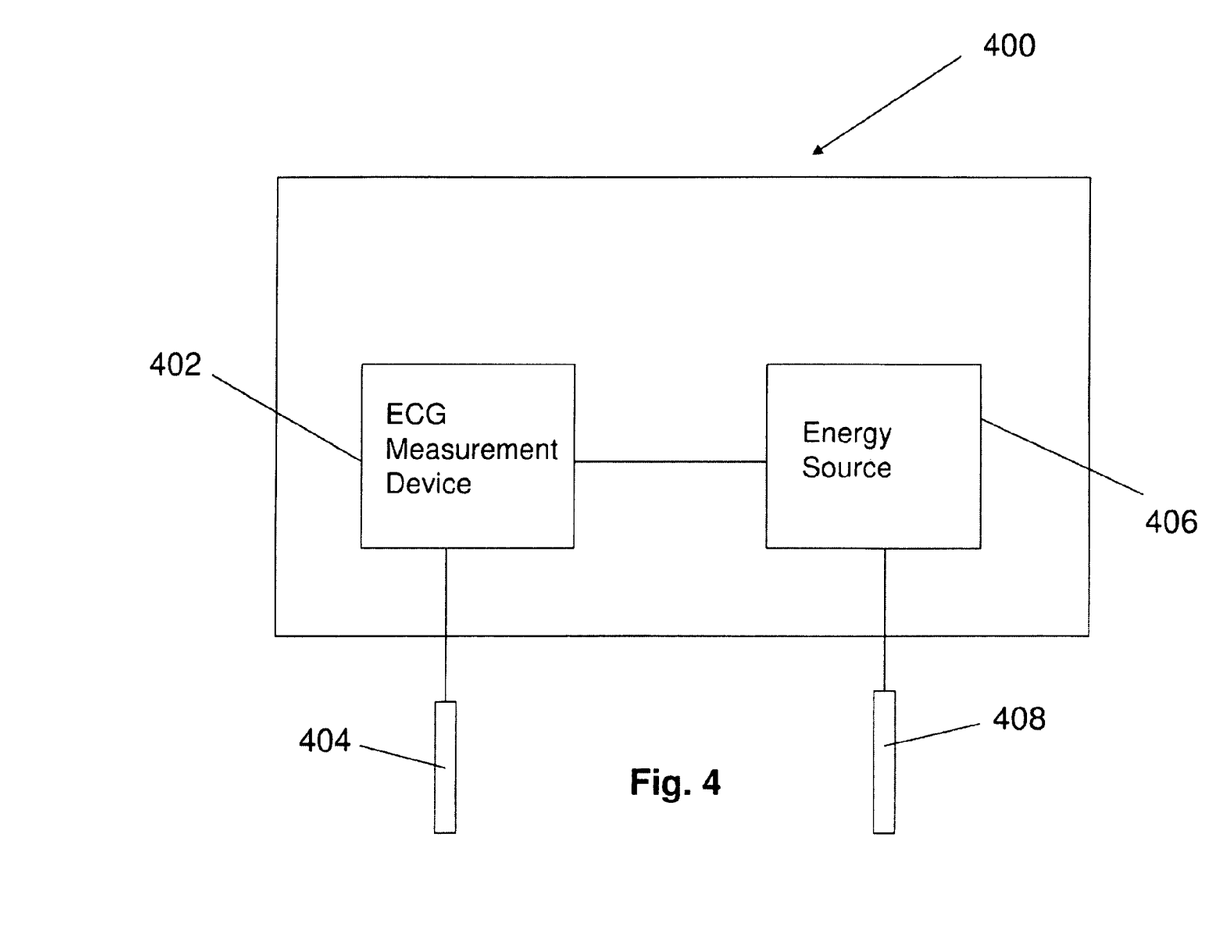
FIG. 4 is a block diagram illustrating an embodiment of a system that may utilized in the present invention.

In some embodiments, the energy source used to generate the energy used for perforation may be operable to communicate with an ECG measurement device, in order to deliver energy automatically in response to the ECG signal, thus obviating the need for user intervention. FIG. 4 shows an illustration of a system 400 incorporating both an ECG measurement device 402 as well as an energy source 406. In some embodiments, system 400 is a single unit, while in other embodiments ECG measurement device 402 and energy source 406 may be housed in separate units but may be operable to communicate with each other. In some embodiments, the communication is bi-directional, while in other embodiments the communication is uni-directional, with energy source 406 receiving trigger signals from ECG measurement device 402 and delivering energy accordingly. FIG. 4 further illustrates an ECG sensor 404 for delivering an ECG signal to ECG measurement device 402. In some embodiments, ECG sensor 404 comprises a plurality of ECG electrodes positioned on the body of a patient for measuring an ECG signal. In alternate embodiments, an ECG mapping catheter is positioned within the heart to measure the ECG signal. In addition, FIG. 4 illustrates a perforation device 408 for receiving perforation energy from energy source 404, as described hereinabove.

In some embodiments, the electrical energy is delivered in relatively short pulses of energy, i.e. the delivery of energy is effected for a time period of less than about 1.0 seconds and, more particularly, for between about 0.2 seconds to about 0.8 seconds. The short duration of energy delivery adds a measure of safety and helps to ensure that the myocardium will not be substantially affected by the energy delivered to create channel 240 through the parietal pericardium.

The user may stop the delivery of energy when energy delivery device 212 has reached pericardial cavity 236, as shown in FIG. 2B. Stopping the delivery of energy when energy delivery device 212 has reached pericardial cavity 236 may ensure that myocardium 228 of the heart is not penetrated by perforation device 200, thus preventing unwanted damage to myocardium 228.

In one embodiment, in order to ascertain when energy delivery device 212 has reached pericardial cavity 236, the energy is delivered for a substantially brief duration, e.g. in pulses, as described hereinabove, with a time period between pulses when substantially no energy is delivered. During any one or more of these time periods when substantially no energy is delivered, the user injects contrast solution through the distal end of perforation device 200. If the distal end of perforation device 200 has not reached pericardial cavity 236, the contrast solution will accumulate in the mediastinum. If the distal end of perforation device 200 is located within pericardial cavity 236, the contrast solution will be seen surrounding the cardiac silhouette, thus providing an indication to the user that the pericardial cavity has been reached. In such an embodiment, each pulse may last less than about 1.0 seconds, more particularly between about 0.2 seconds and about 0.8 seconds, with between about 0.5 seconds and about 5 seconds between each pulse.

In an alternate embodiment, rather than injecting contrast, a user may aspirate fluid between the periods of energy delivery. Upon reaching the pericardial cavity, pericardial fluid will be aspirated, providing confirmation to the user that the pericardial cavity has been reached. In a further embodiment, a user may measure pressure exerted on a distal end of the device, where the pressure exerted may be fluid pressure or pressure exerted by a tissue contacting the distal end of the device. Measuring pressure exerted on the distal end of the device may thus serve as an indication that the distal end is located within the pericardial cavity and may also indicate whether or not the distal end is contacting the epicardium.

In any of the aforementioned embodiments, the means of confirmation, i.e. injection of contrast, aspiration of fluid or measurement of pressure, may be accomplished utilizing the same device that is used to deliver the perforation energy to the pericardium. For example, as described hereinabove, an electrosurgical device defining a lumen longitudinally therethrough may be used both for delivering energy as well as for injection of contrast, aspiration of fluid and/or measurement of fluid pressure exerted on the distal end of the electrosurgical device.

In yet another embodiment, the user may monitor the electrical impedance at energy delivery device 212 to ascertain when at least a portion of energy delivery device 212 has reached pericardial cavity 236. In other words, perforation device 200 may comprise an impedance sensor, which in some embodiments may comprise the energy delivery device itself, which measures the electrical impedance at energy delivery device 212. Due to the presence of fluid in pericardial cavity 236, the outer layers 232, 234, of the pericardium will have different impedances than that seen within pericardial cavity 236. For example, the impedance of the tissue of the outer layers of the pericardium may be greater than about 400 ohms, and the impedance of the pericardial fluid may be between about 100 and about 300 ohms. Thus, if the user monitors the impedance as device 200 is advanced, the user may manually stop the delivery of energy when a change in impedance indicates that energy delivery device 212 is located at least partially within pericardial cavity 236. In a further embodiment, the energy source and perforation device 200 may be operable such that the delivery of energy is automatically stopped when a change in impedance indicates that energy delivery device 212 is located at least partially within pericardial cavity 236.

In another embodiment, the user uses tactile sensation to ascertain, when at least a portion of energy delivery device 212 has reached pericardial cavity 236. In other words, when energy delivery device 212 has penetrated outer layers of the pericardium 232, 234, and has entered pericardial cavity 236, the mechanical resistance felt by the user changes, for example the user may feel less resistance, at which point the user may stop the delivery of energy to avoid unwanted damage to the myocardium.

In a further embodiment, a user visualizes the location of the perforation device using an imaging device positioned in proximity to the perforation device. For example, in some such embodiments, an intracardiac echocardiographic (ICE) imaging catheter is positioned within the heart and is used to visualize the position of the perforation device. Alternatively, an imaging catheter may be positioned within the coronary sinus.

Figure 2C:
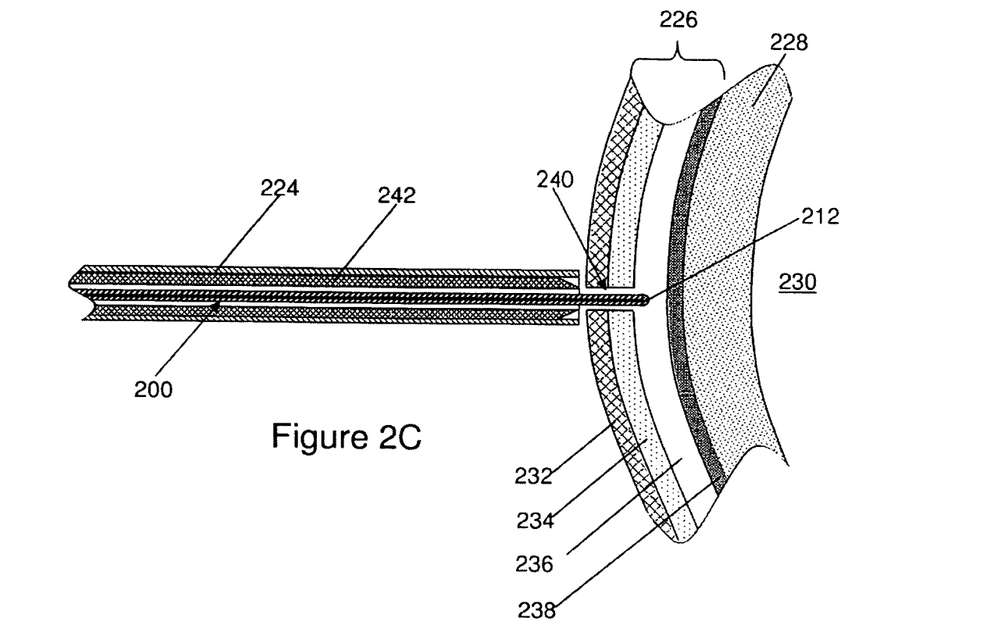
Figure 2D:
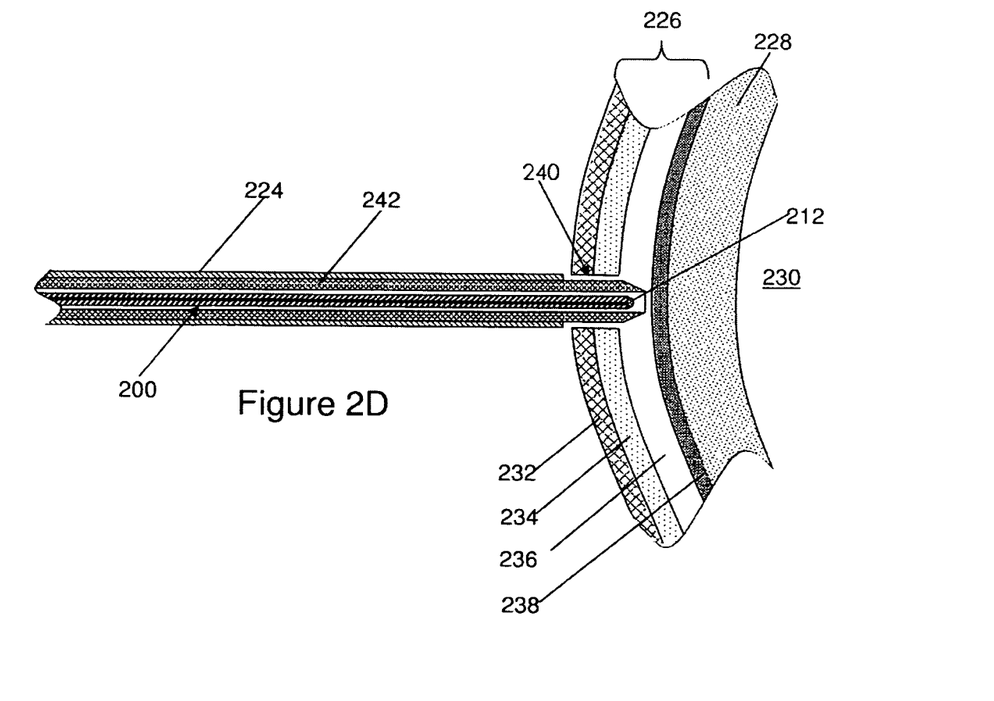

With the distal end of perforation device 200 positioned within pericardial cavity 236, the user may choose to dilate channel 240, and may position a sheath or cannula within channel 240 to maintain patency of channel 240. For example, in some embodiments, a dilator 242 is advanced through cannula 224, and over perforation device 200, as shown in FIG. 2C. The distal region of dilator 242 is advanced through channel 240, such that channel 240 is dilated, as shown in FIG. 2D. Dilator 242 may have a substantially circular and blunt distal end in order to minimize the risk of accidental myocardial perforation. In addition, dilator 240, in some embodiments, is tapered, which allows for a more gradual dilation of channel 240 to help maintain hemodynamic stability.

Figure 2E:
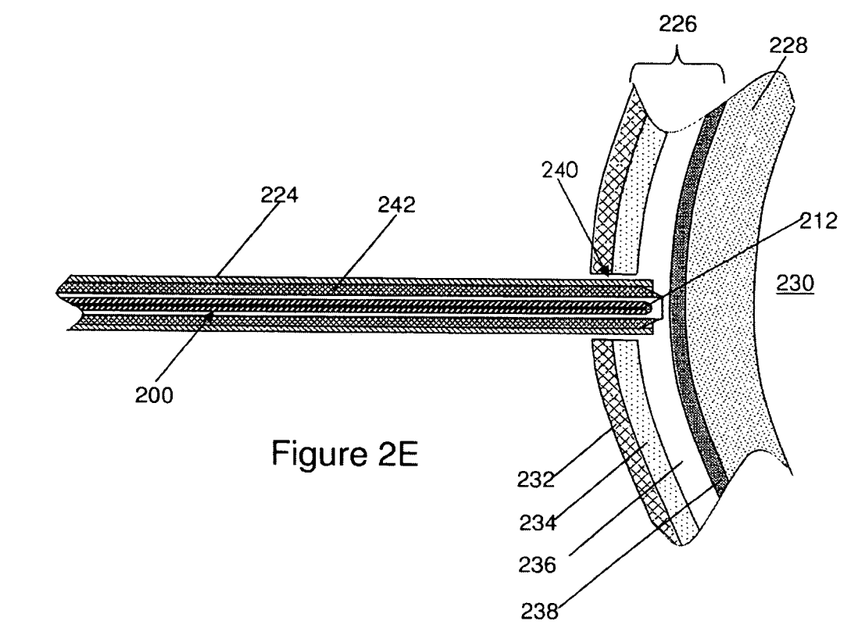
Figure 2F:
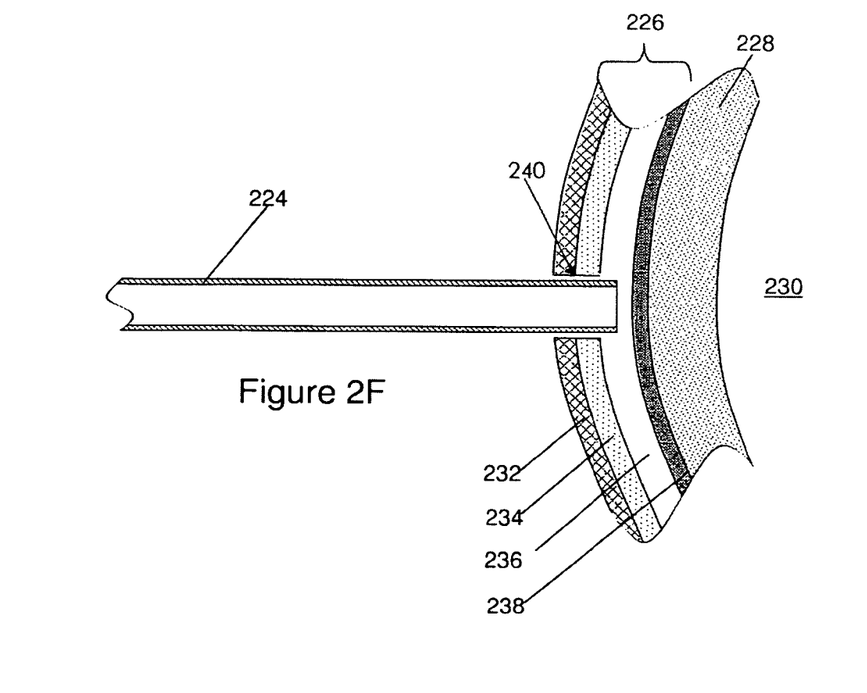

Referring now to FIG. 2E, the distal end of cannula 224 is then, in some embodiments, advanced over dilator 242, into pericardial cavity 236. Perforation device 200 and dilator 242 may then be withdrawn from pericardial cavity 236, if so desired by the user, and removed from the patient's body, leaving only cannula 224 in place in pericardial cavity 236, as shown in FIG. 2F. Cannula 224 may then serve as a conduit for other surgical devices to access the pericardial cavity. In alternate embodiments, a sheath may be advanced through cannula 224, over both perforation device 200 and dilator 242. The distal end of the sheath may be advanced into pericardial cavity 236 along with the distal end of the dilator. The sheath and dilator may be advanced substantially concurrently or at least partially sequentially. The dilator 242, perforation device 200, and cannula 224 may then be removed from the patient's body, leaving only the sheath in place in pericardial cavity 236. The sheath may then serve as a conduit for other surgical devices. For example, a guidewire may be introduced into the pericardial cavity, or a pericardiocentesis needle may be introduced through cannula 224 or the sheath in order to drain fluid may be drained from the pericardial cavity. Alternatively, in embodiments utilizing a separate ablation catheter for epicardial ablation, the ablation catheter may be introduced through cannula 224 or the sheath, and an ablation procedure may then be performed on the myocardium.

In further embodiments, a method of the present invention may be utilized for lead placement in biventricular pacing or for placing other devices that may be helpful for heart failure. Alternatively, embodiments of the method may be used for infusing medications, for example antiarrhythmic agents, directly on the ventricle surface, or to inject growth factors or stem cells to stimulate blood vessel growth or tissue regeneration.

Thus, embodiments of the present invention provide a method for accessing the pericardial space, whereby the risk of damaging the myocardium is substantially reduced. By delivering energy to create a channel through the outer layers of the pericardium to the pericardial space, the user may significantly reduce the risk of perforating the myocardium as may occur when using a needle with mechanical force or when employing a surgical procedure to cut the pericardium.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

I claim:

1. A method of accessing a pericardial cavity of a heart comprising delivering energy via a flexible device to a pericardium in a manner which creates a channel substantially through a parietal pericardium and does not substantially affect myocardial tissue.

2. The method of claim 1, wherein said delivering of said energy is effected for a time period of less than about 1.0 seconds.

3. The method of claim 2, wherein said delivering of said energy is effected for a time period of about 0.2 seconds to about 0.8 seconds.

4. The method of claim 1, wherein said energy is delivered substantially during diastole and is substantially not delivered during systole of a cardiac cycle.

5. The method of claim 1, wherein said energy is delivered in response to a signal indicative of a cardiac cycle of the heart.

6. The method of claim 5, wherein said signal is an electrocardiogram.

7. The method of claim 6, wherein said energy is delivered in response to a P-wave of said electrocardiogram.

8. The method of claim 6, wherein said energy is delivered in response to a T-wave of said electrocardiogram.

9. The method of claim 1, further comprising using a contrast fluid to determine a presence of said channel.

10. The method of claim 9, wherein the contrast fluid is delivered through a device used for delivering said energy.

11. The method of claim 1, wherein a distal end of said device is substantially atraumatic thereby reducing a risk of accidental myocardial puncture or laceration.

12. The method of claim 1, further comprising the steps of:
stopping the delivery of energy;
confirming a location of a distal end of said flexible device; and
repeating the steps of delivering energy, stopping the delivery of energy, and confirming a location of said distal end, until said channel extends to said pericardial cavity.

13. The method of claim 12, wherein said step of confirming a location of said distal end comprises measuring electrical impedance at said distal end.

14. The method of claim 1, wherein said energy is electrical energy.

15. The method of claim 14, wherein said electrical energy is in the radiofrequency range.

16. The method of claim 1, wherein said energy is optical energy.

17. The method of claim 1, further comprising the step of advancing a dilator over said flexible device and into said pericardial cavity.

18. The method of claim 17, further comprising the step of advancing a sheath over said flexible device and said dilator, and into said pericardial cavity.

19. The method of claim 1, further comprising a step of placing at least one cardiac pacing lead.

20. A method of accessing a pericardial cavity of a heart comprising:
(a) delivering electrical energy to a pericardium in a manner which creates a channel partially through a parietal pericardium and does not substantially affect myocardial tissue; and
(b) repeating (a) until a channel is formed substantially through said parietal pericardium.

21. The method of claim 20, wherein said delivering of said electrical energy is effected by an electrosurgical device and further wherein said device is also used for aspirating fluid following (a).

22. The method of claim 20, wherein said delivering of said electrical energy is effected by an electrosurgical device and further comprising measuring pressure exerted on a distal portion of said electrosurgical device prior to (b).

23. A method of epicardial ablation, comprising: delivering electrical energy via an electrosurgical device to a pericardium in a manner which creates a channel substantially through a parietal pericardium to a pericardial cavity and does not substantially affect myocardial tissue; and delivering energy via said electrosurgical device to create a lesion in the epicardium.

24. The method of claim 23, wherein said electrosurgical device comprises at least one perforation electrode for creating said channel and at least one ablation electrode for creating said lesion.

* * * * *